United States Patent
Houtzager et al.

(10) Patent No.: US 8,129,178 B2
(45) Date of Patent: Mar. 6, 2012

(54) BIOREACTOR ASSEMBLY COMPRISING AT LEAST ONE TRAY-LIKE ROCKING PLATFORM

(75) Inventors: Erwin Houtzager, XD Amerongen (NL); Sander Huurman, WJ Renkum (NL)

(73) Assignee: Millipore Corporation, Billerica, MA (US)

( * ) Notice: Subject to any disclaimer, the term of this patent is extended or adjusted under 35 U.S.C. 154(b) by 474 days.

(21) Appl. No.: 11/663,532

(22) PCT Filed: Jul. 1, 2005

(86) PCT No.: PCT/EP2005/007094
§ 371 (c)(1), (2), (4) Date: Jun. 29, 2007

(87) PCT Pub. No.: WO2005/111192
PCT Pub. Date: Nov. 24, 2005

(65) Prior Publication Data
US 2007/0269888 A1    Nov. 22, 2007

Related U.S. Application Data

(60) Provisional application No. 60/630,215, filed on Nov. 24, 2004, provisional application No. 60/655,896, filed on Feb. 25, 2005.

(30) Foreign Application Priority Data

Sep. 22, 2004    (EP) .................................... 04447205

(51) Int. Cl.
*C12M 1/00* (2006.01)
*C12M 3/00* (2006.01)

(52) U.S. Cl. .................................. 435/292.1; 435/305.2
(58) Field of Classification Search ............... 435/292.1, 435/305.2
See application file for complete search history.

(56) References Cited

U.S. PATENT DOCUMENTS
5,423,603 A    6/1995    Reynolds et al.
(Continued)

FOREIGN PATENT DOCUMENTS
JP    07-047255    6/1995

OTHER PUBLICATIONS
International Search Report for PCT/EP2005/007094 mailed Oct. 31, 2005.

*Primary Examiner* — William H Beisner
*Assistant Examiner* — Michael Hobbs
(74) *Attorney, Agent, or Firm* — Nixon & Vanderhye P.C.

(57) ABSTRACT

The present invention relates to a bioreactor assembly containing a reactor frame that permits linear upscaling under identical conditions of culture volumes from two liters to thousands of liters. The bioreactor contains at least one rocking platforms being capable of holding at least one disposable bag adapted for receiving a total volume of at least 2 liters. The at least one platforms have a tray-like shape, that induces the fluid in the bag to move and form a wave-like motion. The at least one platforms are attached to the reactor frame and are positioned on top of each other along a vertical axis. In particular, the weight distribution of the rocking platforms is approximately in balance during rocking. The present invention further relates to methods using the bioreactor assembly.

17 Claims, 8 Drawing Sheets

U.S. PATENT DOCUMENTS

| | | | |
|---|---|---|---|
| 5,674,006 A * | 10/1997 | Islam et al. | 366/239 |
| 5,902,618 A | 5/1999 | Haasis, Jr. et al. | |
| 6,461,853 B1 * | 10/2002 | Zhu | 435/243 |
| 2001/0002985 A1 | 6/2001 | Kleinsasser | |
| 2002/0096930 A1 * | 7/2002 | Bellvis Castillo | 297/423.26 |
| 2002/0155595 A1 * | 10/2002 | Adelberg et al. | 435/308.1 |
| 2007/0128718 A1 * | 6/2007 | Courtois et al. | 435/325 |

* cited by examiner

BIOREACTOR ASSEMBLY COMPRISING AT LEAST ONE TRAY-LIKE ROCKING PLATFORM

This application is the US national phase of international application PCT/EP2005/007094 filed 1 Jul. 2005, which designated the U.S. and claims benefit of EP04447205.8 filed 22 Sep. 2004, U.S. Provisional Appl. No. 60/630,215 filed 24 Nov. 2004, and U.S. Provisional Appl. No. 60/655,896 filed 25 Feb. 2005, the entire contents of each of which are hereby incorporated by reference.

STATE OF THE ART

In the twentieth century, cell cultures have reached industrial proportions. Stainless steel fermentation vessels of several hundreds of thousands liters are not uncommon for the growth of micro-organisms that produce enzymes or secondary metabolites. The methods include batch, fed-batch, continuous or semi-continuous perfusion. Gradually, more challenging cultures such as mammalian, insect or plant cells have been adapted for growth in fermentation vessels using highly specialized media. Although the design of these vessels differs in detail, they have several common features. The cells are kept in suspension by rotating stirring blades placed vertical in the vessel, and gas exchange is facilitated by injection of air, $O_2$ or $CO_2$ at the bottom. Medium composition and pH can be regulated through continuous monitoring and injection of chemical components to adjust such parameters.

There are several drawbacks to this design: the shearing forces that are introduced through the stirring blades and the cavitation of miniscule air bubbles is detrimental to more sensitive cell types or organisms. Also, these vessels have to be rigorously cleaned between production runs to prevent cross-contamination, which is time consuming and needs to be validated for individual cultures. Furthermore, the use of stirred fermentors requires highly trained operators. The cost price for stirred fermentors is high across the whole size range and therefore they are used repeatedly over long periods of time, thus increasing infection risks as a result of mechanical failures. Most importantly, optimization of culture conditions for stirred fermentors at research or pilot scale cannot be transferred in a linear way to commercial scale production. The fluid dynamics, aeration, foaming and cell growth properties change with an order of magnitude when the scale increases. The range of available handbooks, scientific publications and patents on this subject are a good indicator that up-scaling cell cultures from research to production scale requires significant expertise and detailed adaptations of protocols (e.g. K van 't Riet, J Tramper 1991 Basic Bioreactor Design, Marcel Dekker Publ.). For more delicate cell types or organisms, a large scale stirred fermentation vessel is not a viable device, even when more subtle stirring techniques such as airlift fermentors are used.

These drawbacks have led to the development of disposable fermentors. One example of such a disposable fermentator are systems based on wave agitation, solving at least some of the problems described above. For example, with equipment invented by e.g. Singh (U.S. Pat. No. 6,544,788) and Roll (WO 00/66706) it was demonstrated that even fragile cells such as CHO cells (Pierce, 2004 Bioprocessing J 3: 51-56), hybridoma cells (Ling et al., 2003, Biotechn Prog, 19: 158-162) and insect cells (Weber et al., 2002 Cytotechn 38: 77-85) can be grown with sealed plastic bags mounted on a rocking platform. Also anchorage-dependent cells and viruses were grown successfully in wave-agitated disposable bags (Singh, 1999 Cytotechn 30: 149-158). Such disposable units are relatively cheap, decrease the risk of infection because of their single use and require no internal stirring parts as the rocking platform induces wave-like forms in the liquid phase to facilitate gas exchange. This principle cannot be expanded to the size of hundreds of thousands of liters such as the industrial fermentors but are currently available from 1 liter to 500 liters (total bag volume, Wave Biotechnology AG, Switzerland, Wave Biotech Inc, USA). The hydrodynamics of the different bags, however, are different, as a result of the differences in depth and height. Therefore, the use of these bags requires that each step in an up-scaling process needs to be optimized.

SUMMARY OF THE INVENTION

The present invention provides a first bioreactor that permits linear upscaling under identical conditions of culture volumes from two liters to thousands of liters, using disposable bags with wave agitation. The modular and flexible design of the bioreactor allows parallel culturing of different bags in one configuration so that different cultures and culture conditions can be run at the same time. Alternatively, a single bag might be divided into different compartments to allow different conditions to be run at the same time.

The bioreactor was designed to accommodate the growing need of disposable fermentors, and especially the need for up-scaling wave-agitated culture systems. The basic design of the bioreactor has at least one platform or tray. In case of more than one platform or tray, these platforms or trays can be mounted on top of each other. The trays can rock in adjustable angles at an adjustable cycling speed. The vertical design greatly reduces footprint space.

The bioreactor has eliminated problems normally associated with up-scaling biocultures by providing the first linear scaling design. The depth and height of each culture bag, and in particular the ratio between depth and height, is kept constant for all bags, thus maintaining identical hydrodynamics of the wave agitation in all bag sizes. Therefore, an optimized protocol in a small bag translates immediately into even the largest bag. Furthermore, the bioreactor offers the unique option to grow many small volumes in parallel to identify optimal media conditions for a new cell line or the production of a new biological compound. These same conditions can be applied for the full scale production environment.

The bioreactor is suitable for incubating and culturing all kinds of cells, such as mammalian cells, insect cells, plant cells, viruses, micro carrier cultures, yeast, bacteria, starter cultures and more. Furthermore, it allows the culturing of more complex systems, like multicellular systems and organs. The modular design using disposable bags furthermore allows incubating and culturing of cells under different conditions, comprising but not limited to aerobic and anaerobic conditions. Moreover, the use of black bags will allow reactions to occur in the dark, while transparent bags will allow illumination by daylight or light at a certain wavelength.

The bioreactor can also be used for other processes that require a constant mixing of ingredients to prevent sedimentation as is required in separation processes. In general, rocking can be performed when other ways of mixing like stirring or bubbling are not possible. Examples for these processes are well known in the art and comprise dissolving, homogenizing, incubations including enzymatic incubations, separations e.g. based on affinity, emulsifications, and fermentation. Also for these processes, the modular design using disposable bags allows these processes to occur under different conditions, such as the application of high or low oxygen pressure, anaerobic conditions, inert gasses etcetera.

On top of this, the modular design using disposable bags allows the conditions to be variable during these processes thereby permitting delicate processes to occur.

Advantages

The bioreactor according to the present invention has several advantages over single unit rocking bioreactors. Only one electric motor and speed-regulatory unit is required, all rocking platforms have the same speed and/or rocking angle, the entire assembly has an efficient small footprint, especially when more than one platforms are placed on top of each other along a vertical or near-vertical axis. The small footprint also allows for easy containment of the entire assembly in one room that can be made gas-tight for sanitary reasons and can be temperature controlled.

The parallel design of the assembly, providing for example 16 units with 70 liters total volume per unit such as described in a preferred embodiment of this invention, has advantages over larger volume single unit bioreactors. First, once culture conditions are optimised for a single unit, there are no further changes needed for scaling-up, a well known problem when increasing the size of a bioreactor itself. In the bioreactor of the present invention, up-scaling can be achieved either by increasing the number of platforms on top of each other, or simply by increasing the width of the assembly.

Besides the advantage of linear scalability, the parallel unit approach decreases the risk of culture failures, thereby increasing the reliability of the total production. This is especially important when using biological organisms that are notoriously difficult to grow and where still unknown biological parameters may hamper production or where unwanted infections occur with relatively high frequency, e.g. as a result of complex medium requirements, intracellular infection sources or mechanical failures.

Another advantage of the parallel design is the possibility to optimise and test culture conditions directly at production scale. The preferred embodiment described in this invention allows 16 different conditions to be tested in the same run, or with minor alterations 32 or 48 or even 64 different culture conditions, without altering the wave form and thus the fluid dynamics and gas exchange properties of the rocking bioreactors, parameters that have influence on the culture conditions and with this invention only need to be optimised once before up scaling. Also, different cell lines can be run in parallel, each producing e.g. a different recombinant protein.

The bioreactor assembly is designed to hold disposable culture bags, and the combination of this assembly and disposables holds further advantages. The down-time between production runs, necessary for cleaning and sanitation, is significantly reduced compared to glass or stainless steel vessels. The expertise level of operators can be reduced compared to those that monitor classical fermentors. Furthermore, the use of disposable bags strongly eliminates cross-contamination to occur and limits the need for quality-control validation during and between runs.

FIGS. 1-4 show some of the possible devices that are part of this invention.

DESCRIPTION OF THE INVENTION

In the present specification and the appended claims, the singular forms "a", "an", and "the" include plural references unless the context clearly dictates otherwise. Unless defined otherwise, all technical and scientific terms used herein have the same meaning as commonly understood to one of ordinary skill in the art.

The bioreactor assembly according to the invention comprises a reactor frame and at least one rocking platform (6) attached to the reactor frame, said platform capable of holding at least one disposable bag adapted for receiving a total volume of at least 2 liters, or 5 liters. If more than one rocking platform is used, said rocking platforms are positioned on top of each other along a vertical axis (v) (see FIGS. 1, 2 and 3), or a near-vertical axis (not shown). Alternatively, said more than one platforms are mounted opposite to each other in a horizontal plane. The bioreactor assembly may take a variety of configurations. The reactor frame comprises vertical poles (7), supporting beams (8), one or more horizontal beams (10), open grooves (9) and/or a ground plate. As used herein, and with reference to a preferred embodiment, a bioreactor assembly is shown having a front side (FIGS. 1 and 3, frontal view), a rear side and two lateral sides, due to the relative positions in the illustration. In FIG. 2, a lateral side view of a preferred embodiment is shown. In a preferred embodiment, the rocking platforms (6) are mounted between two vertical poles (7). The assembly can be made rigid by one or more horizontal beams (10) between the vertical poles (7). Supporting beams (8) on either or both sides of the assembly can be attached to the vertical poles (7). The vertical poles (7) and/or the supporting beams (8) can be secured to the floor, which should be strong enough to carry the weight of the assembly, preferably without inducing vibrations. In addition or in the alternative, the vertical poles (7) and/or the supporting beams (8) of the bioreactor can be attached to a rigid ground plate. In a further embodiment, the vertical poles are secured via the ceiling. It will be apparent to the person skilled in the art that the assembly can be made mobile by attachment of wheels under the vertical poles (7), the supporting beams (8) and/or the ground plate. In addition, the assembly may contain one or more open grooves (9) for holding tubes, etc. The dimensions of the bioreactor assembly are open to wide variations, according to the need of the user. In particular, the dimensions of the reactor frame are determined by the dimensions of the rocking platforms. The reactor frame can be made of any material suitable to support the weight of the bioreactor assembly as a whole, including the bags, their contents, and the forces exerted by the rocking, and are well known to the person skilled in the art. The bioreactor can be made, for example from light materials like aramid and carbon fiber, but are preferably made of a material chosen from the group consisting of steel, aluminium or stainless steel.

Each of the rocking platforms of the bioreactor assembly are adapted to rock along a horizontal axis in a single degree of freedom (tilting), for instance as illustrated in FIG. 2. The axis of rotating is a bearing-fitted axis (4) by which the rocking platforms (6) are attached to the reactor frame, e.g. vertical pole (7). Preferably, the tilting of the rocking platforms induces and sustains a wave-like motion in the bags. As such, the present invention relates to a bioreactor assembly as described herein, further comprising a means for rocking each of the platforms. Each of said platforms can rock along a horizontal axis in a single degree of freedom, whereby rocking of the platform induces the fluid in the bag to move and form a wave-like motion. The means for rocking the platforms may comprise an electrically powered motor (1), a gear box (Z) and a transmission system (2, 3, 4, 5, 11) to transfer the rotational movement of the motor into the tilting of the platforms. Preferably, the motor (1) is mounted on the reactor frame, e.g. on top of the reactor frame, such as on vertical pole (7) or horizontal beam (10). In a further embodiment, the motor (1) is not mounted on the reactor frame, but only connected with the reactor frame via a transfer system. For instance, the motor can also be placed on the floor and/or in a room different from the chamber in which the reactor frame is placed, such as outside a containment chamber comprising the reactor frame and rocking platforms, e.g. for sanitary, safety or maintenance reasons. Accordingly, the bioreactor assembly according to the invention is further characterized in that said means for rocking the platforms comprises an electrically powered motor (1) such as, for instance, a frequency regulated electromotor or a single stepless electronic motor, such as a frequency regulated 1.5 kW electronic motor. Frequency regulated electromotors, also known as AC Variable Frequency Drives (VFD) or DC Variable Speed Drives (VSD) can be obtained from manufacturers such as ABB (Switzerland), Siemens (Germany), Lenze (Germany) and Fincor (USA). The motor (1) is connected via a gearbox (Z) to the first connecting bar (2). The first connecting bar (2) can have a range of attachment points to the gear wheel of gear box (Z), allowing the rotational movement of the motor to be transferred to a movement to and fro in one plane, e.g. into a horizontal axis of oscillation. Preferably, the rocking angle of the platforms ranges from a full cycle to between about +10 to +30 degrees and −10 to −30 degrees, even more preferably between about of +15 and −15 degrees. As such, the present invention relates to a bioreactor assembly as described herein, further characterized in that the means for rocking each of the at least one platforms is adapted for rocking each of the platforms in a single degree of freedom through a predetermined angle in the range of between −15° and +15° relative to a horizontal position of the platform.

A full moving cycle or movement cycle is defined herein as a full cycle or rotation of the driving axe, possibly transferred via a gearbox connected to the electromotor, which drives the rocking platforms from any starting position up, down and back up, or down, up and back down, until the same position as the starting position is reached. The circular movement of the motor is transferred via three different bars or tumblers (2, 3, 5) via heavy duty bearings to the rocking movement of the platforms. Type one connecting bar (2) can be attached to the gearbox (Z) at several positions, thereby effectively influencing the rocking angle, e.g. between maxima of +15 and −15 degrees. The bearing for connecting axe (11), attached to connecting tumbler (3), may be placed vertical above the bearings of the axes (4) that carry the rocking platforms (6). The rotational movement of the motor (1) may be transferred to both lateral sides of the reactor frame by a connecting axis (14), preventing torsion of the structure. It will be apparent that in case the rotational movement is transferred to both lateral sides, both lateral sides comprise a similar, e.g. identical, transmission system. It will thus be apparent to the person skilled in the art that the rocking platform is movably attached to the reactor frame. In other words, the rocking platform is capable of moving in a single degree of freedom relative to the reactor frame.

The rate and the amplitude of the rocking action of the platform can be controlled and adjusted to provide optimum conditions for a wave like motion of the medium or the bioreactions to occur. The angle through which the platform rocks to and fro can easily be adjusted either by changing point of attachment of type one connecting bar (2) to the gear wheel of gear box (Z), varying the diameter and point of attachment of the gear wheel of the gear box, or by varying the length of the connecting bar (2).

In another embodiment, a bioreactor assembly as described herein is characterized in that said means for rocking the platforms is adapted for maintaining the weight distribution of said platforms approximately in balance during a movement cycle. Because the circular movement of the motor drives the rocking platforms, the momentum of the movement of all platforms must be 360 degrees or a multiplicity thereof. This means that two platforms can be mounted such that they differ about 180 degrees in their phase of the movement, while three platforms differ about 120 degrees, meaning 0 degrees, 120 degrees, and 240 degrees in the movement cycles for each of the platforms, respectively. For instance, it will be appreciated that in case five platforms are used, the momentum of 3 platforms is about 360 degrees while the momentum of the remaining 2 platforms is also 360 degrees. Alternatively, each of the five platforms differs about 72 degrees, meaning, about 0 degrees, about 72 degrees, about 144 degrees, about 216 degrees and about 288 degrees in the movement cycles for each of the platforms, respectively. This is to keep balance to the system. For example, if a first platform is tilted +15 degrees, a second platform is tilted −15 degrees, and when said first platform moves down to −15 degrees, at the same time, the second platform moves up to +15 degrees, with the same amplitude but in the opposite phase as the first platform. It will be apparent that preferably said platforms are approximately the same, or having approximately the same weight distribution and centre of gravity.

Alternatively, said platforms are approximately kept in balance during a movement cycle by random distribution of the movement cycles for each of the platforms. If more than 5 platforms are attached to the reactor frame, random movement of the platforms, i.e. the momentum of the movement of the platforms differs from each other, may keep the bioreactor in balance. The person skilled in the art will appreciate that the reactor frame may be reinforced in case the balance is compromised.

In yet another embodiment, said means for rocking the platforms is adapted such that each of the platforms can be halted during a run while the other platforms remain in motion.

The rocking platforms (6) can be mounted on bearing-fitted axes (4) which can be attached to the vertical poles (7). The at least one rocking platforms are positioned on top of each other. The bearing-fitted axes (4) are aligned along a vertical axis (v). The rocking platforms (6) are designed to hold disposable bags. The bioreactor assembly according to the invention comprises between 2 and 20 rocking platforms, for instance 2, or 3, or 4, or 5, or 6, or 7, or 8, or 9, or 10, or 12, or 14, or 16, or 20 rocking platforms positioned on top of each other along a vertical axis.

Alternatively, the at least one rocking platforms can be positioned pair wise opposite to each other on two, or more, vertical or near vertical poles.

The dimensions of the at least one rocking platforms are amenable to wide variations. Preferably, the dimensions of the rocking platforms tolerate a wave-like motion in the bags. As such, the present invention relates to a bioreactor assembly as described herein, characterized in that the depth (x) of said rocking platforms (6) or trays can have any size between 0 and 5 meters, but preferably has a dimension between about 0.5 m and about 1.2 m, and more preferably about 0.85 m, e.g. 83 cm. The width (y) of the rocking platforms (6) or trays can have a dimension between about 0.4 m and 8 m, preferably about 3 m. In this regard, the depth (x) is the distance from the front side to the rear side of the rocking platform, while width (y) is the distance from one lateral side to the opposite lateral side of the rocking platform. The rocking platforms have a lower surface and a substantially flat top surface. The top surface of said rocking platforms is adapted for carrying bags.

The rocking platform may contain various, i.e. at least two, spatially defined regions or compartments. Each compartment is individually addressable for selectively holding at least one bag. The compartments are such that contact between adjacent compartments is prevented. The compartments may be rectangular, but any suitable discrete form may be used. Accordingly, the present invention relates to an assembly as described herein, wherein the rocking platforms are divided into compartments.

The present invention relates particularly to a bioreactor assembly comprising a reactor frame and at least one rocking platform attached to the reactor frame, said at least one platform being capable of holding at least one disposable bag adapted for receiving a total volume of at least 2 liters, characterized in that said at least one rocking platform comprises a tray-like shape such that rocking of the platform induces the fluid in the bag to move and form a wave-like motion.

The top surface of the rocking platforms may have extensions protruding upwards perpendicular to the top surface of said rocking platforms, also on the outer boundaries of the platforms. The said extensions may form a tray-like structure, e.g. with a width of about 74 cm, a depth of about 83 cm and a height of about 20 cm (tray). Accordingly, the present invention relates to an assembly as described herein, wherein said rocking platforms may have a tray like shape. The tray-like shape or structure may support the positioning of the bags during rocking. It will be apparent that said tray-like structure may be divided into compartments. As such, the present invention relates to a bioreactor assembly as described herein, further characterized in that said tray or tray-like structure contains at least one insert. Said inserts may divide the tray into compartments and may support the positioning of the disposable bag during rocking.

Each platform is adapted for holding at least one bag. It will be apparent that if the size of the bags is reduced, each platform may hold more than one bag. For instance, the bioreactor assembly according to the invention may comprise 1 to about 24 bags per platform, and preferably 1, or 2, or 3, or 4, or 6, or 8, or 9, or 12, or 15, or 16, or 18, or 20, or 24 bags per platform.

Preferably, the bags are disposable. The bags can be pressurized via a gas inflow and a restricted gas outflow. The bags may have an overpressure relative to the atmospheric pressure. This maximal overpressure will depend on strength of the individual bags and is in principal unlimited.

The form of the pressurized bags determines the formation of a proper rolling wave of the liquid when the tilting of the platform changes direction. In most cases, the pressurized bag takes the form of a flattened balloon. A proper form of the bags can be dictated by the platform itself, which can have a tray-like shape (see FIG. 4). Although the platform in FIG. 4 contains straight sides, it is particularly emphasized that platforms with curved sides are also part of this invention.

If the bag size is slightly too large for the dimensions of the rocking platform, and the bag tends to take up the square form of the rocking platform, an inlay (13) can be placed inside the rocking platform along the front and rear side to achieve a proper curving of the culture bag which in turn will changes the hydrodynamics of the rolling wave.

Alternatively, a proper form of the bag supporting a wave-like motion can be achieved by, for instance, the intrinsic properties of the bag. A rounded form on the frontside and backside (rear side) of the pressurized culture bag will induce a proper rolling wave when the rocking of the platform changes direction.

Another way of supporting a correct form of the bags is by reinforcing straps around the body of the bag, which are not or minimally expandable, or by extrinsic means, such as mounting an external support device on the top of the bag, such as, for instance, clamps or a solid lid (12). The lids may help keeping the bags into their position. Furthermore, the lids may provide a force downwards on the bags, whereby the bags adapt a conformation supporting a wave like motion of the fluids when rocking. Accordingly, the present invention relates to an assembly as described herein, further characterized in that said tray further comprises at least one lid.

The solid lids (12) may have open slits, for instance of about 5 cm wide, allowing access to tubing connectors that can be sealed into the disposable bags. The disposable tubings for medium input, inoculation, air in- and outflow, sampling ports and monitoring sensors (when required) can be connected using standard connectors such as luer locks that are commonly used, to tubings that are placed in the open groove (9) and that connect to the necessary pumps, monitoring equipment or downstream processing devices. In another embodiment, the rocking platforms may comprise a hole, for instance at the front side of the platform and extending from the top surface to the bottom surface of the rocking platform, through which tubes can be connected to allow easy harvesting of the culture, when said front side of the platform, and consequently also the bag, is tilted downwards.

Each of said bags may have a total volume of about between 2 and 500 liters, preferably between about 5 and 300 liters, or more preferably, between 20 and 200 liters, and even more preferably between 50 and 100 liters, and most preferably about 70 liters. Alternatively, 2 bags of about 35 liters, or three bags of about 20 liters would also be suitable. In the present invention, the total volume of a bag is defined as the volume of the liquid medium and the gas-filled headspace combined.

Sterilized disposable bags such as described for this bioreactor assembly are widely available. These comprise sterilized empty bags, or bags pre-filled with sterile dry powdered media, or bags pre-filled with sterilized liquid media. These bags can easily be customized by the suppliers for the required placing and size of tube connectors (e.g. Cambrex Inc USA, Stedim USA, Millipore USA, Wave Biotechnology, Switzerland). The disposable bag material is chosen dependent on the culture requirements and can range from simple PE plastic foils or composite PE/PP foils to laminated plastic materials of different origin (PE/PP/EVA/nylon etc.) of which the innermost foil does not interact chemically with the content of the bag, e.g. there should be no diffusion of plastic softeners into the medium, absorption of hormones to the foil, they should be pyrogen-free etc. The foils can be sealed via heating devices that are commonly known in the art, with a length and width that is appropriate for the unit size on the rocking platforms. Bags can be manufactured in registered, class 10.000, cleanrooms and can be inspected for leakage prior to use, for example using ASTM-F2095-01 certified tests (FDA Federal Register).

The bags according to the invention are particularly suited for sustaining, growing or culturing micro organisms, cells or small organisms. Accordingly, the present invention relates to a method for culturing micro organisms, cells or organisms in disposable bags. In particular, the present invention relates to a method for parallel culturing of micro organisms, cells or organisms in disposable bags, comprising the steps of:
(a) introducing a growth medium and a culture sample into a bag, and preferably at least two bags,
(b) mounting said bag(s) onto the rocking platform or trays of a bioreactor assembly as described herein, and possibly disperse the bags over the plafform(s),
(c) rocking the platform or trays in a single degree of freedom to thereby induce a wave motion to the liquid media in the bag;
wherein the order of steps (a) and (b) can be interchanged, e.g. reversed. As such, the present invention relates to a method as described supra, wherein the rocking of the platforms is set at a predetermined rate in the range of about 1 to 60 rocks per minute, preferably between 10 to 45 rocks per minute, or more preferably between 20 to 30 rocks per minute. Preferably, the rocking of the platforms induces and sustains a wave motion of the liquid medium in the bag.

Without limitation, the cells used for culturing can be of animal, mammalian, avian, reptilian, fish, amphibian, human, arthropod, annelid, insect, sponges, nematode, plant, fungal, yeast or microbial origin. It will be appreciated that method according to the invention relates to cells used for the production of viruses, including bacteriophages.

The bioreactor is suitable for incubating and culturing all kinds of cells, such as mammalian cells, insect cells, plant cells, viruses, micro carrier cultures, yeast, bacteria, starter cultures and more. Furthermore, it allows the culturing of more complex systems, like multicellular systems and organs. The modular design using disposable bags furthermore allows incubating and culturing of cells under different conditions, comprising but not limited to aerobic and anaerobic conditions.

The bioreactor can also be used for other processes that require a constant mixing of ingredients. In general, rocking can be performed when other ways of mixing like stirring or bubbling are not possible. Examples for these processes are well known in the art and comprise dissolving, homogenizing, incubations including enzymatic incubations, separations e.g. based on affinity, emulsifications, and fermentation. Accordingly, the present invention relates to a method for parallel incubating or homogenizing ingredients in disposable bags, comprising the steps of:
(a) introducing a liquid medium and at least one other component into the disposable bags, and
(b) mounting said bags onto the rocking platforms or trays of a bioreactor assembly as described herein, and
(c) rocking the platforms or trays in a single degree of freedom to thereby induce a wave motion to the liquid media in the bag;
wherein the order of steps (a) and (b) can be interchanged.

Also for these processes, the modular design using disposable bags allows these processes to occur under different conditions, such as the application of high or low oxygen pressure, anaerobic conditions, inert gasses etcetera.

On top of this, the modular design using disposable bags allows the conditions to be variable during these processes thereby permitting delicate processes to occur.

The whole bioreactor assembly can be built inside a temperature controlled chamber for heating or cooling the culture media, or the rocking platforms can be installed with widely available flat, thermostated heating elements or mats on which the culture bags can be placed. A temperature controlled chamber can easily be made gastight in case fumigation must be possible as a safety measure when pathogenic organisms are grown.

In a final embodiment, the present invention relates to the use of a bioreactor assembly as described supra for culturing, and preferably parallel culturing of micro organisms, cells or organisms.

It will be apparent to the person skilled in the art that the bioreactor assembly described herein can be configured and reconfigured to accommodate a wide variety of needs.

The main feature that discriminates a reactor assembly according to the present invention from other bioreactors known in the art, is that this reactor assembly allows the linear scaling up from small volumes of about 2 liters, to large volumes up to 500 liters, without further need to optimize each new culture volume.

The following detailed depiction of a preferred embodiment is offered by way of illustration and not by way of limitation.

DETAILED DEPICTION OF A PREFERRED EMBODIMENT

Figure 1:
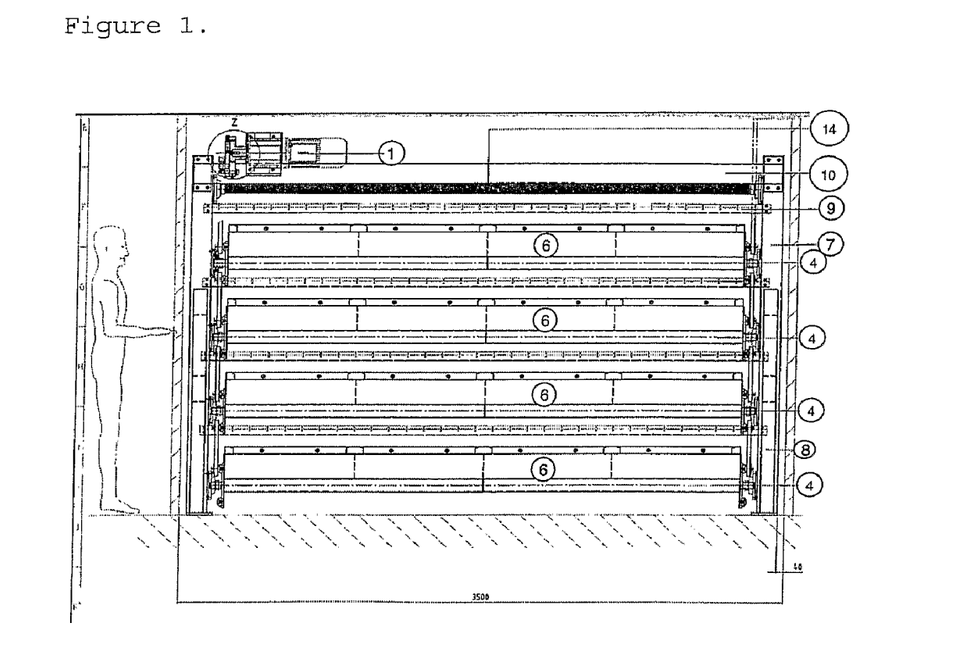
FIG. 1. Front side of the preferred embodiment
FIG. 2. Lateral side of the preferred embodiment
FIG. 3. Mini bioreactor
FIG. 4. Platform shape
FIG. 5. Polyacrylamide gel showing iMab expression
FIG. 6. Relative optical density of the 4 bags in the linear scale up.
Figure 2:
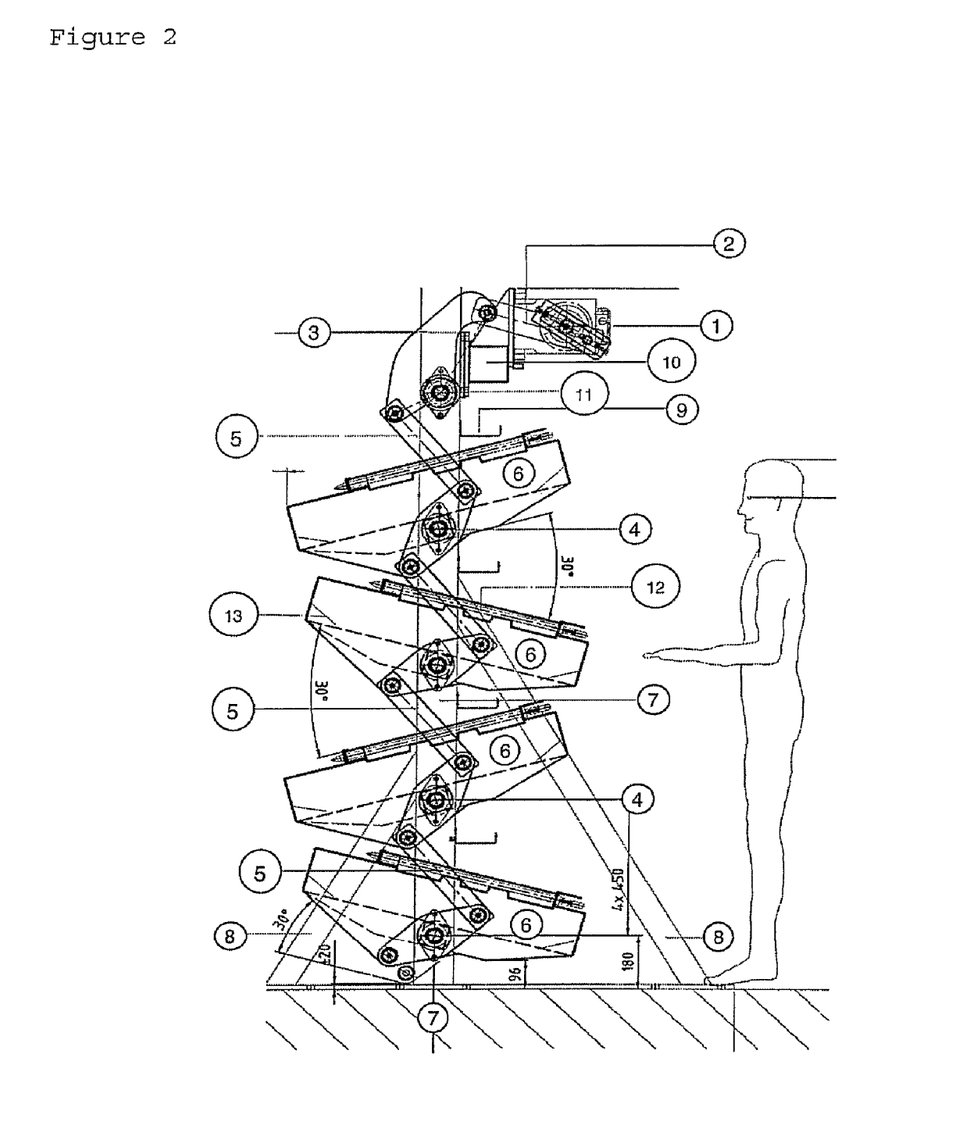
Figure 3:
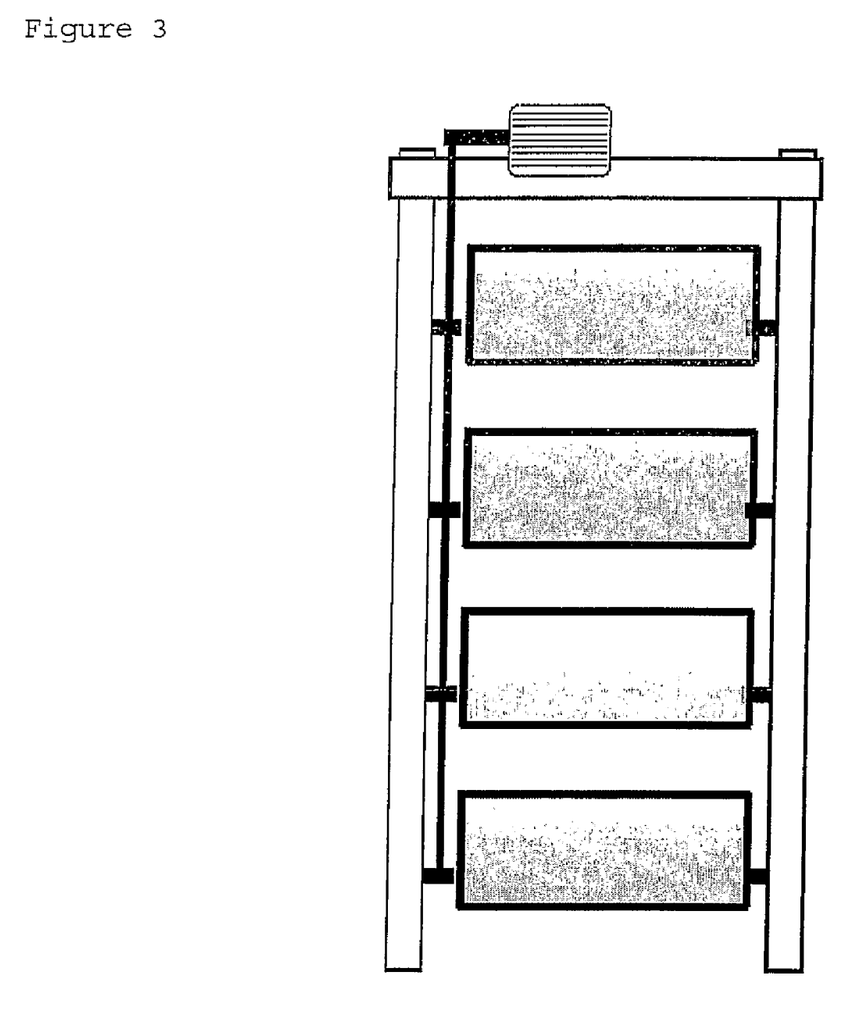

FIGS. 1 (frontal view) and FIG. 2 (side view) outline a preferred embodiment of the general design of the bioreactor assembly. Four rocking platforms (6), holding a total of 4×4 units for disposable culture bags are mounted between two vertical poles (7) on top of each other in such a way that they are always in a balanced position, with a maximum angle of 30 degrees between adjacent platforms. A frequency regulated 1.5 kW electronic motor (1) with an attached gearbox (Z) is placed on top of the reactor frame. The motor is connected via a gearbox (Z) to the first connecting bar (2), which has a range of attachment points, thus allowing the circular movement of the motor to a movement in one plane in such a way that the rocking angle of all platforms range from anywhere between 10 and 30 degrees. The rocking movement is transferred via three different bars or tumblers (2, 3, 5) comprising heavy duty bearings. Bar (2) can be attached to the gearbox at several positions, thereby effectively influencing the rocking angle between maxima of +15 and −15 degrees relative to a horizontal axis running through platform carrying axe (4). The central bearing of platform carrying axe (11) in tumbler (3) is placed vertical above the bearings of the axes (4) that carry the rocking platforms (6). The assembly is made rigid by a horizontal beam (10) between the vertical poles (7) and supporting beams (8) attached to the vertical poles. The rocking movement is transferred to the side opposite the motor by a connecting axis (14) from where a similar set of bars and tumblers transfer the movement to all rocking platforms. Both items (7) and (8) are secured to the floor.

Figure 4:
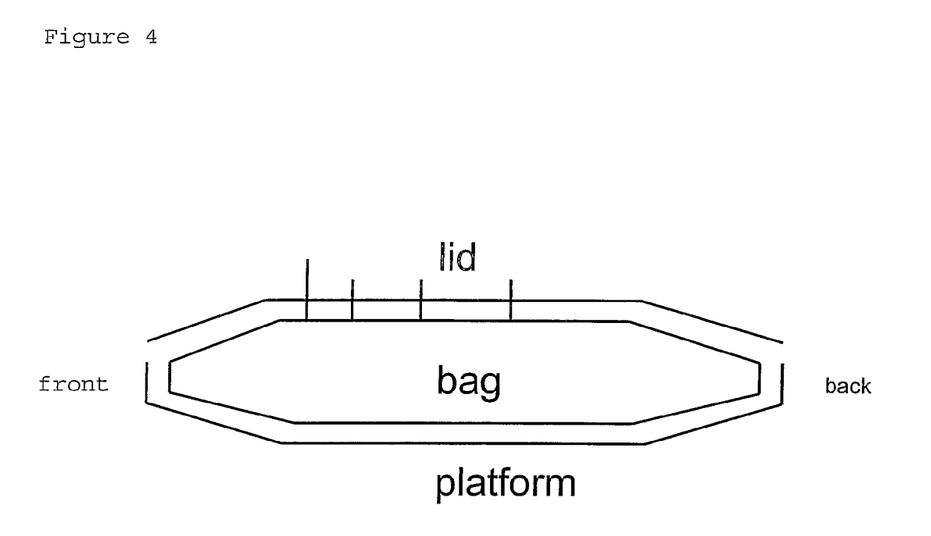

The rocking platforms (6) are mounted on the bearing-fitted axes (4), are designed to hold the disposable culture bags, and have a depth of 83 cm and a height of 20 cm. Preferably, the platform has a tray-like shape, as shown in FIG. 4, such that rocking of the platform induces the fluid in the bag to move and form a wave-like motion. The width is dependent on the number of disposable bags that are placed on one platform and the length of the platform. In the example, the unit width is 74 cm, with a total platform width of 300 cm holding four units (see FIG. 2), capable of holding a bag size of 80 cm width and 90 cm deep. Once disposable bags are placed inside the holding units, they are covered by solid lids (12) that have open slits of ca. 5 cm wide allowing access to the tubing connectors that are sealed into the disposable bags. The disposable tubings for medium input, inoculation, air in- and outflow, sampling ports and monitoring sensors (when required) are connected using standard connectors to tubings that are placed in the open groove (9) and that connect to the necessary pumps, monitoring equipment or downstream processing devices. Also on the bottom side of the rocking platform a hole is placed through which tubes are connected to allow easy harvesting of the culture when that side of the bag is tilted downwards. The disposable bags are pressurized via the gas inflow and a restricted gas outflow and will take the form of a flattened balloon once the lid (12) is secured in place.

| Legend to FIGS. 1 and 2 |
| --- |
| 1) stepless electric motor |
| 2) type one connecting bar |
| 3) connecting tumbler |
| 4) platform carrying axe running in bearings |
| 5) type two connecting bar |
| 6) rocking platform |
| 7) vertical pole |
| 8) support beam |
| 9) open cable and tubing groove |
| 10) horizontal support beam |
| 11) bearings for connecting axe |
| 12) covering lid |
| 13) inlay (optional) |
| 14) connecting axe |
| z) gear box. |

EXAMPLES

Example 1

Applications for Bioreactor

In this example, several micro-organisms were grown on the bioreactor of the present invention. These culture micro-organisms of interest were *Rhizobium radiobacter* (Young, J. M., Kuykendall, L. D., Martinez-Romero, E., Kerr, A. & Sawada, H. (2001). *Int J Syst Evol Microbiol* 51, 89-103; ATCC 19358) and Arthrobacter histidinolovans (Skerman, V.B.D., McGowan, V., and Sneath, P.H.A. (1980). (editors). *Int. J. Syst. Bacteriol.*, 30, 225-420; ATCC 11442).

*Rhizobium radiobacter* was grown using the bioreactor in 5 liter bags filled with 0.8 liter of 0.5*LB broth (containing 2.5 g/l Yeast extract, 5 g/l Pepton, 2.5 g/l NaCl) supplemented with 50 microliter per liter antifoam 204 (Sigma) at 29° C. and 20 rpm. The culture was grown under continuous aeration using an airpump. The culture was innoculated at OD 1.3 (600 nm) from an overnight (~24 hours) culture grown in shaker flasks at 29° C. and 225 rpm. The culture density was monitored during culturing by measuring the optical density (OD) at different time points as an indicator of the growth of the micro-organism.

In analogy to *Rhizobium radiobacter*, *Arthrobacter histidinolovans* was grown in the bioreactor in 5 l bags filled with 0.8 liter of 0.5*LB broth supplemented with 50 microliter per liter antifoam 204 (Sigma) at 29° C., 20 rpm. The culture was grown under continuous aeration using an aeration pump. The culture was innoculated at OD 1.0 (600nm) from a overnight (~24 hr) culture grown in shaker flasks at 29° C. and 225 rpm. The culture density was monitored during culturing by measuring the optical density (OD) at different time points as an indicator of the growth of the micro-organism.

The results of both the *Rhizobium radiobacter* and the *Arthrobacter histidinolovans* cultures are shown in Table 1. It is clear from this Table that this bioreactor is very suited for the cultivation of both types of bacteria.

TABLE 1

Optical density of the *Rhizobium radiobacter* and *Arthrobacter histidinolovans* cultures

| T(min) | OD 600 nm |
| --- | --- |
| *Rhizobium radiobacter* | |
| 0 | 1.3 |
| 120 | 1.9 |
| 240 | 6 |
| 360 | 10 |
| 450 | 15 |
| 615 | 15 |
| *Arthrobacter histidinolovans* | |
| 0 | 1 |
| 120 | 2.4 |
| 240 | 5.6 |
| 360 | 8.6 |
| 450 | 13 |
| 615 | 13 |

Example 2

Expression of iMAb Protein in *E. coli*.

Figure 5:
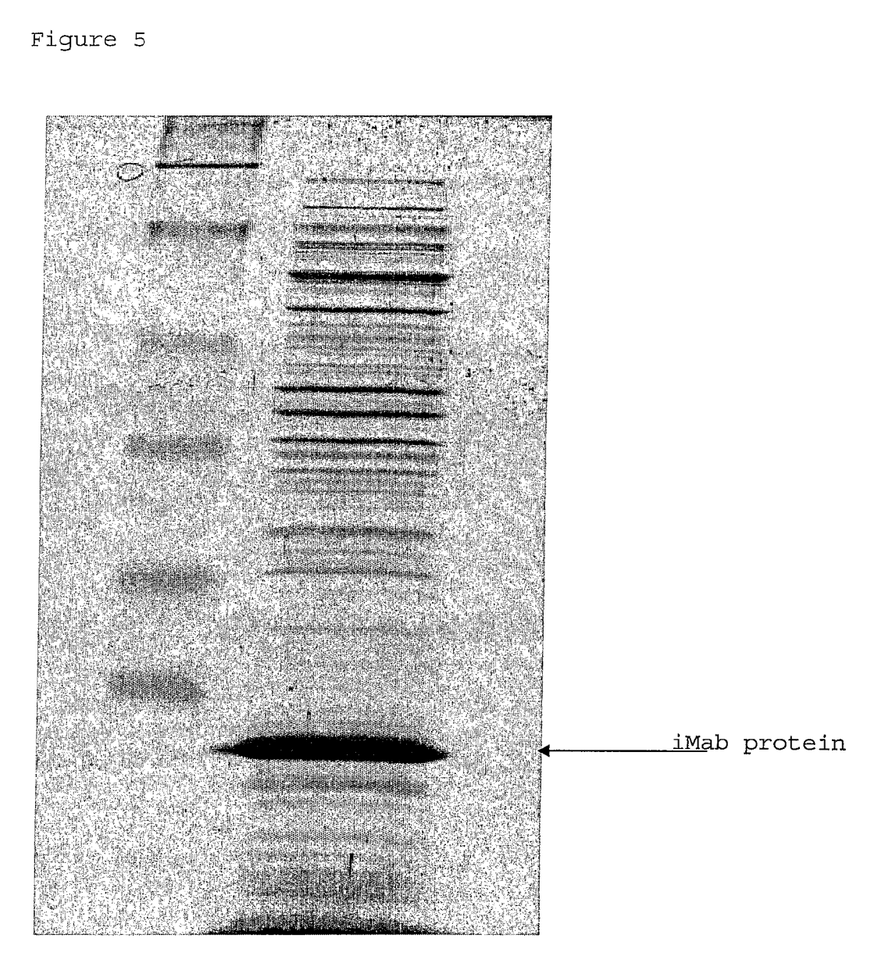

To investigate the use of the bioreactor for protein production in *E. coli*, *E. coli* BL21 (Al) (Novagen) was transformed with the expression vector CM 126-iMAb (vector is described in W003050283) which is based on pET-12a (Novagen). Cells were transformed with the vector by electroporation and grown in shaker flasks overnight at 37° C., 225rpm. Thereafter, cells were innoculated at OD 0.1 (600 nm) in 35 l of medium containing 3*TY medium (24 g/l tryptone, 15 g/l yeast extract, 5 g/l NaCl), supplemented with 50 microliter per liter of antifoam 204 (Sigma) and carbinicillin (100 microgram/ml) in 70 liter (total volume) bags on the bioreactor at 30° C., 40 rpm. Isopropylthio-β-galactoside (IPTG) was added to a final concentration of 1 mM together with 0.2% arabinose to initiate protein expression when OD 0.9 (600 nm) was reached. The culture was continuously aerated using an aeration pump. The cells were harvested approximately 4 hours after the addition of IPTG and concentrated using hollow fiber technology (at a cut off of 400 kD) and concentrated pellets were stored at −20° C. until use. Protein expression was analyzed by Sodium Dodecyl Sulphate PolyAcrylamide Gel Electrophoresis (SDS-PAGE, see FIG. 5). Wet and dry weight of the cells was determined and total protein expression was calculated. The OD of the culture was not very high, because of the bacterial induction system used. It is concluded that *E. coli* cells, expressing iMab protein were very efficiently grown in the bioreactor, with an excellent expression level of 40% of total protein (see FIG. 5). Especially the ease at which the 35 l volume culture could be grown on the bioreactor without further optimization combined with an excellent expression of proteins is very beneficial.

| Details of this culture are: | |
|---|---|
| Total culture volume: | 35 l |
| OD600 nm: | 7.6 |
| Cell wet weight: | 5.87 g/l |
| Cell dry weight: | 1.38 g/l |
| Total protein: | 0.69 g/l |
| iMab expression: | 40% of total protein |
| iMab production: | 0.28 g/l |
| Total iMab in 35 L batch: | 9.8 g |

Example 3

Linear Scalability

To investigate the linear scale-up characteristics of the Bioreactor for protein production in E. coli, E. coli BL21 (Dab 3) (Novagen) was transformed with the expression vector CM 126-iMAb (described in W003050283) which is based on pET-12a (Novagen). Cells were electro orated with the vector and grown in shaker flasks containing 100 ml 3see culture media (24 g/l soy tone, 15 g/l yeast extract, 5 g/l NaCl) supplemented with 4.5% (wavy) glucose and 100 microgram/ml carbenicillin. Cultures were incubated o/n at 37° C., 225 rpm.

To enlarge the seed volume for the linear scale-up, the shaker flask culture was used to inoculate a 13 liter bag, containing 5 liters of culture medium (identical to shaker flasks). After OD 1.5 (600 nm) was reached, this culture was concentrated by hollow fiber technology, with a membrane cut-off size of 400 kDa, surface area 3100 cm$^2$, crossflow speed 180 L/h at 14.5 psi, transmembrane pressure 10 psi.

The bag volumes tested in the linear scale-up experiment were 3, 8, 12, and 40 liters. The filling percentage of all bags was 50%. All the bags had an identical length. The liquid height level was kept identical by varying the width (breadth) of the bags. The identical length and liquid height helped to ensure that the agitated wave was identical in all bags.

Figure 7:
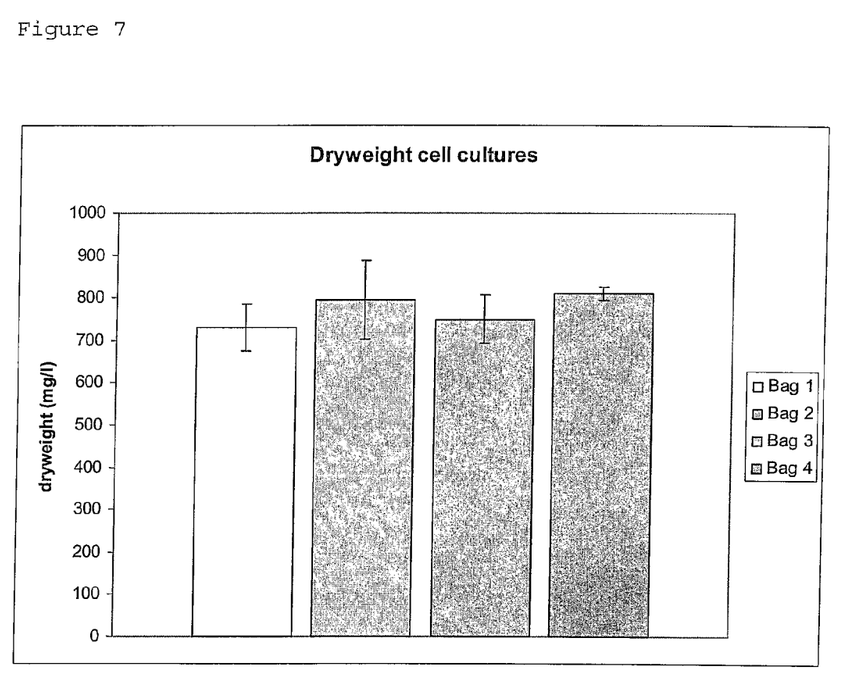
FIG. 7. Dry cell weights determined in duplicate of the final samples at t=960 minutes.
Figure 8:
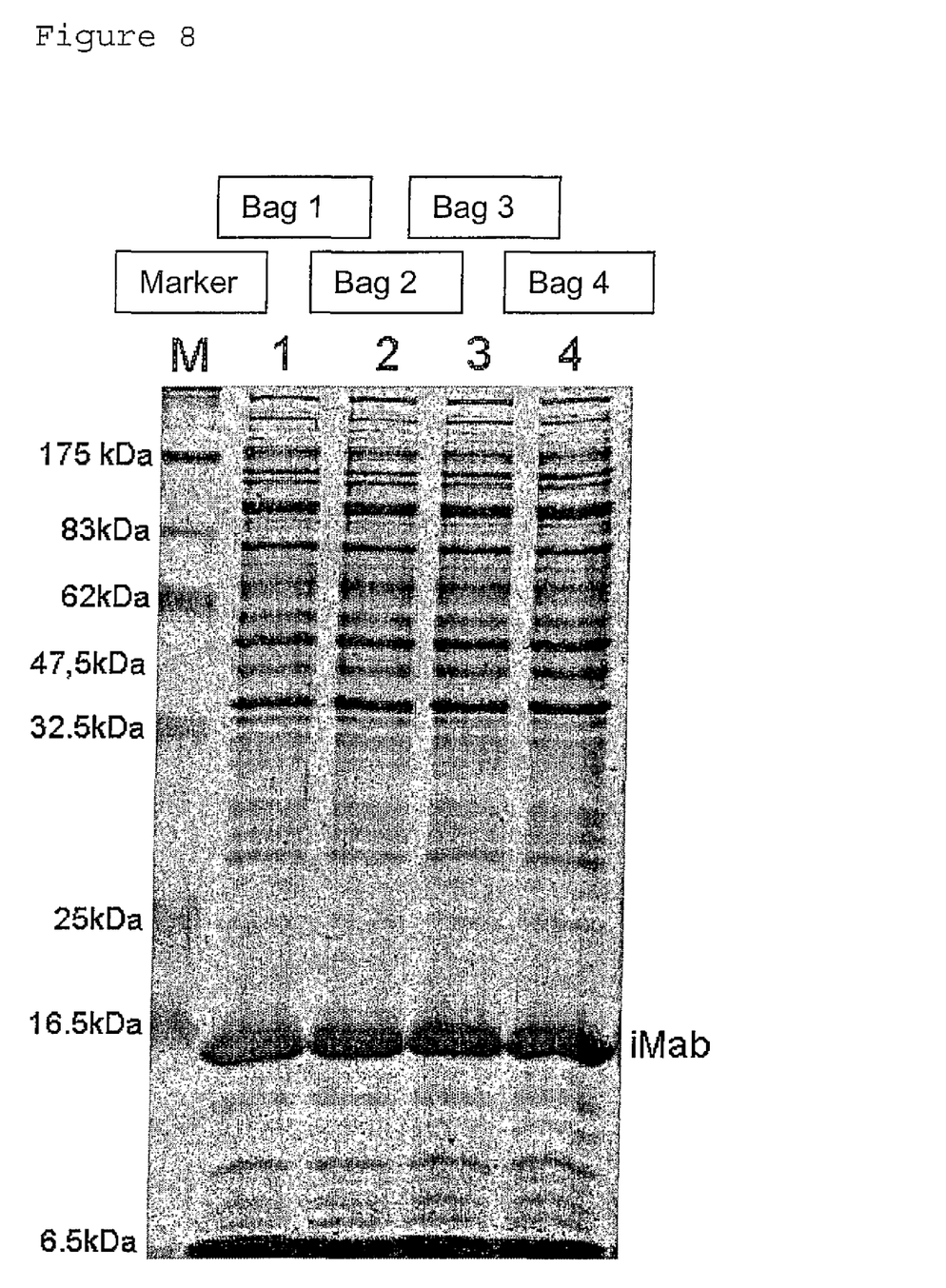
FIG. 8. SDS-PAGE analysis of the final culture samples (t=960 minutes). Gel was stained with Coomassie Brilliant Blue.

The bags were filled with 0.2 μm filter sterilized 3x SY culture medium supplemented with 50 microliter per liter antifoam 204 (Sigma) and 100 microgram/ml carbenicillin. Prior to inoculation, the bags were preheated at 37° C. The bags were inoculated with the concentrated cells at starting OD of 0.1. The cell cultures were incubated at 37° C., with a rocking angle of 12°, and a rocking speed of 40 rocks/minute. The culture was continuously aerated using air cylinders (20% 02, 80% N$_2$) at a flow of 1 liter per minute per 10 liters of culture volume. Samples were taken from each bag at T=0, 105, 235, 325 and 960 minutes after inoculation. From the collected samples, the OD (600 nm) and pH were determined (see FIG. 6, and Table 2). The cells were harvested at 980 minutes after inoculation. Of the final samples, protein expression was analyzed by Sodium Dodecyl Sulphate Poly-Acrylamide Gel Electrophoresis (SDS-PAGE, see FIG. 8). Dry weight of the cells was determined in double and total protein expression was calculated (see FIG. 7).

TABLE 2 pH of different time samples for Bag 1 to Bag 4

| | Time (minutes) | | | | |
|---|---|---|---|---|---|
| | 0 | 105 | 235 | 325 | 960 |
| Bag 1 (3 l) | 6.8 | 6.8 | 7.1 | 7.2 | 9 |
| Bag 2 (8 l) | 6.8 | 6.8 | 7.2 | 7.3 | 8.8 |
| Bag 3 (12 l) | 6.8 | 6.9 | 7.3 | 7.2 | 8.9 |
| Bag 4 (40 l) | 6.8 | 6.8 | 7.2 | 7.5 | 8.9 |

Figure 6:
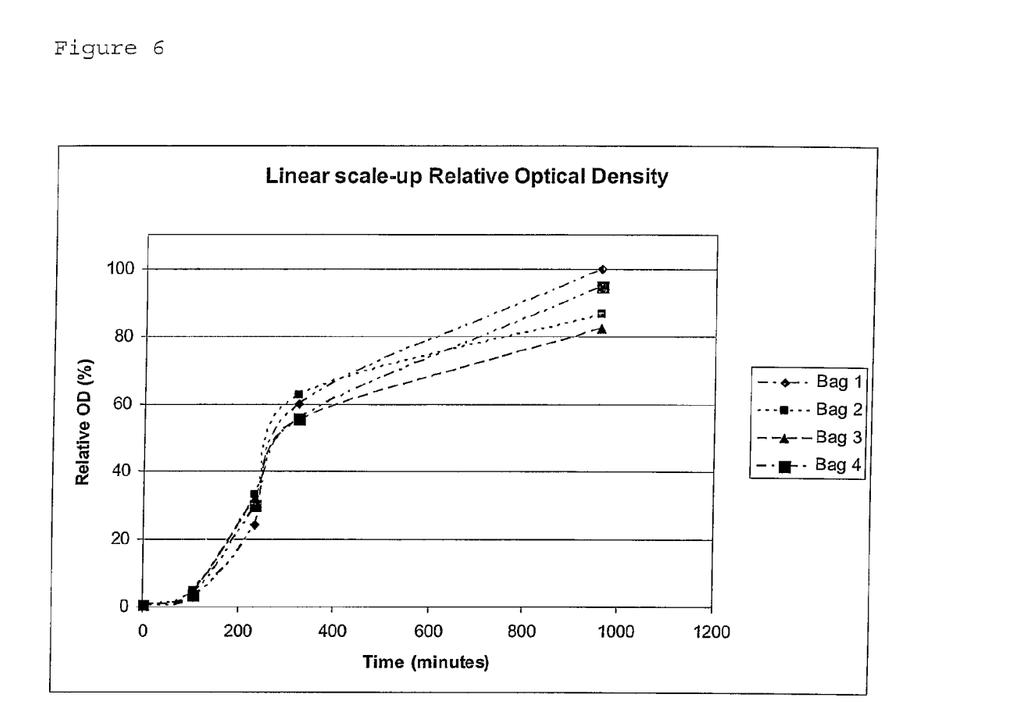

The ODs of the 4 bags were similar in all bags at all time points (FIG. 6). Until t=325 minutes the OD are almost overlapping, although there is some difference at the final point, which is not volume related (maximal difference is 20%). The pH of the cultures was very similar over time, as is concluded from Table 2. The final time points differ no more than 0.2 in pH.

The measured dry weights (FIG. 7) of the final samples of the four bags indicate a mean dry weight of approximately 775 mg/liter culture volume. The dry weight of all final samples were almost similar, within a 10% margin. The iMab expression analysis in FIG. 8 culminates the previous findings with respect to OD, pH and dry weight. The iMab protein expression is almost identical in the four bags as was visible in the gel and was estimated to be ~25% of total E. coli proteins, indicating the linearity in scale up of cultures using the Bioreactor.

The invention claimed is:

1. A bioreactor assembly comprising a reactor frame and at least two rocking platforms attached to the reactor frame, said at least two platforms being capable of holding at least one disposable bag adapted for receiving a total volume of at least 2 liters, characterized in that the movement of the platforms is adapted for maintaining the weight distribution of said platforms approximately in balance during a movement cycle, wherein the at least two platforms move in a same amplitude but in opposite phase to the one or more platforms adjacent to it, each of said rocking platforms being positioned on top of each other along a vertical axis and said one platform relative to the next vertically adjacent platform provided on the same vertical axis rotates in an equal and opposite direction.

2. The bioreactor assembly according to claim 1, further comprising a means for rocking each of said at least one platforms along a horizontal axis in a single degree of freedom.

3. The bioreactor assembly according to claim 1, wherein each of the at least two platforms travel in a single degree of freedom in the movement cycle at least a predetermined angle in the range of between −15 degrees and +15 degrees relative to a horizontal position of the platform.

4. A method for parallel culturing of micro organisms, cells or organisms in disposable bags, comprising the steps of:
   (a) introducing a growth medium and a culture sample into at least two bags,
   (b) mounting said bags onto the rocking platforms of a bioreactor assembly according to claim 1, and
   (c) rocking the platforms in a single degree of freedom to thereby induce a wave motion to the liquid media in the bag;
   wherein the order of steps (a) and (b) can be interchanged.

5. The method according to claim 4, wherein said cells are chosen from the group consisting of animal cells, mammalian cells, avian cells, reptilian cells, fish cells, amphibian cells, human cells, arthropod cells, sponge cells, annelid cells, insect cells, nematode cells, plant cells, fungal cells, yeast or microbial cells.

6. The method according to claim 5, wherein said cells are used for the production of viruses, including bacteriophages.

7. A method for parallel incubating or homogenizing ingredients in disposable bags, comprising the steps of:
(a) introducing a liquid medium and at least one other component into the disposable bags, and
(b) mounting said bags onto the rocking platforms of a bioreactor assembly according to claim 1, and
(c) rocking the platforms in a single degree of freedom to thereby induce a wave motion to the liquid media in the bag;
wherein the order of steps (a) and (b) can be interchanged.

8. The method according to claim 4, wherein the rocking of each of said at least one platform is at a predetermined rate set in the range of about 1 to 60 rocks per minute, preferably between about 10 to 30 rocks per minute.

9. A bioreactor assembly comprising a reactor frame and at least two rocking platforms attached to the reactor frame, the at least two platforms being capable of holding at least one disposable bag adapted for receiving a total volume of at least 2 liters, wherein the movement of the at least two platforms is caused by a motor selected from the group consisting of a frequency regulated motor and a single stepless electronic motor, each of said at least two rocking platforms being positioned on top of each other along a vertical axis and move in a same amplitude but in opposite phase as the platform vertically adjacent to it provided on the same vertical axis in the movement cycle.

10. The bioreactor assembly of claim 9, wherein each of the at least two platforms travel in a single degree of freedom in the movement cycle at a predetermined angle in the range of between −15 degrees and +15 degrees relative to a horizontal position of the platform.

11. The bioreactor assembly of claim 9, further comprising a gear box and a transmission system to transfer the rotational motion of the motor into the rocking motion of the at least two platforms.

12. The bioreactor assembly of claim 9, wherein there are three or more platforms.

13. The bioreactor assembly of claim 9, wherein there are five platforms.

14. The bioreactor assembly of claim 9, further comprising the at least two platforms with curved sides and having a device for achieving a proper curving of the bag so as to create a proper rolling wave when in the movement cycle.

15. The bioreactor assembly of claim 9, further comprising the at least two platforms maintaining the bag in a form to create a proper rolling wave when in the movement cycle and the at least two platforms have a tray shape to maintain the bag in a form to create a proper rolling wave when in the movement cycle.

16. The bioreactor assembly of claim 9, further comprising the at least two platforms maintaining the bag in a form to create a proper rolling wave when in the movement cycle and the at least two platforms have an inlay placed inside each platform along a rear and front side to achieve the proper curving of the bag.

17. The bioreactor assembly of claim 9, further comprising the bag of each of the two or more platforms having a rounded form on a frontside and backside to maintain the bag in a form to create a proper rolling wave when in the movement cycle.

* * * * *